United States Patent [19]

Sugar et al.

[11] Patent Number: 4,482,535

[45] Date of Patent: Nov. 13, 1984

[54] COSMETIC PREPARATION FOR TEETH

[76] Inventors: András Sugar, Törökvész u. 95-97, H-1025 Budapest; Laszlo Fabry, Tartsay u. 28, H-1126 Budapest, both of Hungary

[21] Appl. No.: 387,859

[22] PCT Filed: Oct. 2, 1981

[86] PCT No.: PCT/HU81/00039

§ 371 Date: May 28, 1982

§ 102(e) Date: May 28, 1982

[87] PCT Pub. No.: WO82/01128

PCT Pub. Date: Apr. 15, 1982

[30] Foreign Application Priority Data

Oct. 3, 1980 [HU] Hungary ............................ 2423/80

[51] Int. Cl.$^3$ ...................... A61K 7/16; A61K 31/74; A61K 31/78

[52] U.S. Cl. ........................ 424/49; 424/78; 424/81

[58] Field of Search ................ 424/49, 78, 80, 81

[56] References Cited

U.S. PATENT DOCUMENTS

| | | | |
|---|---|---|---|
| 3,621,079 | 11/1971 | Leeds | 424/80 |
| 3,914,405 | 10/1975 | Shepherd et al. | 424/81 |
| 4,032,627 | 6/1977 | Suchan et al. | 424/49 |
| 4,102,992 | 7/1978 | Davis | 424/49 |
| 4,134,930 | 1/1979 | Kubota | 260/875 |
| 4,150,485 | 4/1979 | Lee et al. | 260/998.11 |
| 4,226,848 | 10/1980 | Nagai et al. | 424/78 |
| 4,250,163 | 2/1981 | Nagai et al. | 424/78 |
| 4,360,605 | 11/1982 | Schmitt et al. | 424/81 |
| 4,362,842 | 12/1982 | Masuhara et al. | 424/78 |

FOREIGN PATENT DOCUMENTS

| | | |
|---|---|---|
| 1309209 | 3/1973 | United Kingdom . |
| 1424034 | 2/1976 | United Kingdom . |
| 518218 | 6/1976 | U.S.S.R. . |

OTHER PUBLICATIONS

Chem. Abst. 86, 34297(e)–(1977)–Loctite Corp.
Chem. Abst. 89, 152,746(y)(1978)–Crisp et al.
Chem. Abst. 94, 71544(g)(1981)–Dreyer-Jorgensen.

*Primary Examiner*—Douglas W. Robinson
*Attorney, Agent, or Firm*—Karl F. Ross; Herbert Dubno

[57] ABSTRACT

The subject of the invention is a cosmetic preparation for teeth which is composed of one or more film-forming polymers—at least one of which is water soluble, partly soluble, emulsifiable or dispersible—and coloring agents. The composition ensures the aesthetic appearance of the teeth and can—by contrast with earlier products—be removed easily and rapidly.

1 Claim, No Drawings

COSMETIC PREPARATION FOR TEETH

STATE OF THE ART

In the dental therapeutical field, polymers are known which can serve as replacement for tooth enamel or for filling cavities in teeth. The significance of these compositions is that they adhere very well to teeth and their hardness reaches or approaches the hardness of the tooth enamel. These enamels, lacquers and the like are applied in dental technology workplaces or clinics and it is not possible to remove them at desired times. These coatings or replacements can last in general up to three years. Commercially numerous compositions are sold, these compositions being applied in solvents so that the polymerization is in part effective upon the tooth surface. For such adhesive dental plastics, generally polyurethane lacquers (e.g. Bayer D 520, Epoxylite 9070, Elmex Protector), polystyrene polymers (e.g. Tubulitec), polyethylmethacrylate polymers or copolymers (e.g. Orthonite) or glycidylmethacrylate copolymers (e.g. Epoxylite 9075, Nuva Seal Espe 71 730 and 717) are used.

The foregoing compositions primarily serve for therapeutics and have a long lasting effect. However, it is in many cases desirable to cosmetically improve the appearance of the teeth only for a brief period as, for example, in the entertainment industry, in theaters, in filming, in television, etc. In such cases, it is desirable to use a composition which will remain only for a short period upon the teeth and can readily be removed therefrom but which will ensure a desirable appearance. It is also very important in such cases to be able to apply the composition at various times and places, i.e. without the intervention of a dentist or technological operations.

THE ESSENCE OF THE INVENTION

The object is achieved with the cosmetic composition of the invention in that the composition is easily handled, can be applied by anyone, the applied coating dries rapidly and, depending upon the composition, remains on the teeth for a period of several hours to several days and from the surface of the teeth can be removed without any difficulty. The hardness of a coating and as a result the time to separation can be varied in accordance with requirements.

PREFERRED EMBODIMENT OF THE INVENTION

The cosmetic tooth composition of the invention comprises one or more film-forming polymers or copolymers—of which at last one is a water-soluble, limitedly soluble, emulsifiable or dispersible polymer—and a coloring agent, and advantageously polymer from monomers or prepolymer corresponding to the film-formed polymer and, if desired, aromatics or other auxiliary substances.

The film-forming polymer can be any nontoxic polymer. Methacrylic acid, methyl-methacrylic acid and their esters, polymers and copolymers of urethanes and styrenes, glycidylmethacrylate polymers and copolymers can advantageously be used. If desired, the composition can contain the polymers together with polymerization catalysts or initiators, and monomers corresponding to the polymer. These film-forming polymers are not soluble in water although they form dispersions in water.

As water-soluble or limitedly soluble polymers, preferably polyvinylacetate, polyvinylpyrrolidone or a polyvinylmethyl ester can be used. As hygroscopic substance glycerine can be used instead of the foregoing.

Polyvinylacetate with a molecular weight of about 100,000, containing 20% acetate and also polymethyl esters which increase adhesion, can preferably be used.

The coloring agent employed in the composition can be any nontoxic coloring agent with good covers; in the case of a further [white] color, titanium dioxide is advantageously used.

If desired, the composition can contain aromatic substances to ensure a pleasant sensation and these can be any nontoxic and acceptable aromatic [aromatizing] agent, preferably menthol. The composition can also use a fluorine-releasing compound as has been used with tooth replacements.

The composition is preferably applied in the form of a dispersion in a solvent which can be formed by any nontoxic liquid, as for example ethanol and/or water. The drying period depends upon the solvent.

The lifespan of a composition [on the teeth] depends clearly upon the proportion of the film-forming agents and the water-soluble polymer. These proportions can be varied within a wide range. The proportions can be varied to provide adhesion times between about two hours and several days. If during use eating occurs or the layer is mechanically utilized it is advantageous to provide a composition with a longer adhesion time while in the case where low mechanical stresses are applied, the adhesion time of several hours may be advantageous.

The coating can be simply removed since, after the appropriate time, the film layer can be readily drawn off the teeth without rubbing and like mechanical operations. Since the hardness of the layer can be much less than the hardness of the tooth enamel, the tooth enamel is not damaged.

In the following the production of an advantageous composition is given:

To 4 mmol sodium dodecylsulphonate is added 100 ml water and nitrogen gases bubble through the solution for a period of ten minutes. Thereafter 0.25% potassium or ammonium persulphonate are added to the solution and the solution is heated with agitation to a temperature of 60° to 70° C. At the upper temperature and with agitation, a methacrylic acid—methyl ester/styrene mixture (90:10) is added drop by drop to the solution until the solution has a gel consistency (about 100 grams). After cooling, 0.5% polyvinyl alcohol and titanium dioxide are added to the dispersion (PVAL 420) and the mixture is homogenized.

If a harder coating is desired the starting material during mixture uses instead of water glycidylmethacrylate and a benzoyl peroxide catalyst is added to the dispersion. The reaction is carried out in this dispersion.

We claim:

1. A method for improving the appearance of the teeth for only a brief period of time between several hours and several days which comprises the steps of:
   (a) applying to the surface of a tooth a cosmetic tooth composition which consists essentially of:
      (1) a first film-forming polymer, said film-forming polymer being emulsifiable and dispersible in water and consisting essentially of a methacrylic acid methyl ester-styrene mixture in a weight ratio of 90:10;

(2) a second film-formng polymer, said second film-forming polymer being water-soluble and consisting essentially of polyvinyl alcohol wherein the weight ratio between the first and second film-forming polymer is 100:0.5;
(3) a titanium dioxide coloring agent; and
(4) a nontoxic solvent selected from the group consisting of water, ethanol, and mixtures thereof;

(b) allowing the film layer to dry; and
(c) drawing off the film layer without rubbing after said brief period of time has elapsed.

* * * * *